United States Patent [19]

Harris, Sr. et al.

[11] 4,094,197

[45] June 13, 1978

[54] SEMI-AUTOMATIC AND AUTOMATIC FLUID INJECTORS

[76] Inventors: Rano J. Harris, Sr., 1945 Carolyn Sue Dr., Baton Rouge, La. 70815; Rano J. Harris, Jr., 5443 Stonewall Dr., Baton Rouge, La. 70816; Julius P. Averette, Jr., 4332 Delaware, Baton Rouge, La. 70805

[21] Appl. No.: 817,817

[22] Filed: Jul. 21, 1977

[51] Int. Cl.² .............................................. G01N 1/12
[52] U.S. Cl. ................................................. 73/423 A
[58] Field of Search ................... 73/422 GC, 423 A; 141/130; 23/259

[56] References Cited

U.S. PATENT DOCUMENTS

| 4,006,654 | 1/1977 | Harris | 73/423 A |
| 4,038,874 | 8/1977 | Baldin et al. | 73/423 A |

*Primary Examiner*—S. Clement Swisher
*Attorney, Agent, or Firm*—Llewellyn A. Proctor

[57] ABSTRACT

An apparatus for sampling and injecting measured liquid samples into the septum inlet of an analytical instrument or the like. Three sub-assemblies comprising the apparatus are (a) an injector inclusive of a barrel communicating with a hollow needle at one end for injecting fluid into through a septum and a valve communicating with the other end for interrupting flow through the barrel and needle, (b) a feed assembly inclusive of an upwardly directed probe for puncturing the septum of an inverted sample containing receptacle for supplying gas pressure to the receptacle and for transporting the sample through a conduit to the valve of the injector, (c) a magazine inclusive of a pair of concentric slidable tubes, the outer tube guiding the inner and the inner adapted to carry the inverted sample receptacle downwardly for puncturing by the probe of the feed assembly so that, the fluid contents of the vial pressurized by injection of gas into the vial via the gas inlet conduit and fluid specimen transported via the fluid specimen outlet to the barrel, whereby on the ingress of an initial portion of the fluid specimen the barrel and needle can be purged and cleaned, a measured quantity of the fluid specimen then trapped, and then injected on insertion of the dispensing end of said needle into said medium.

23 Claims, 13 Drawing Figures

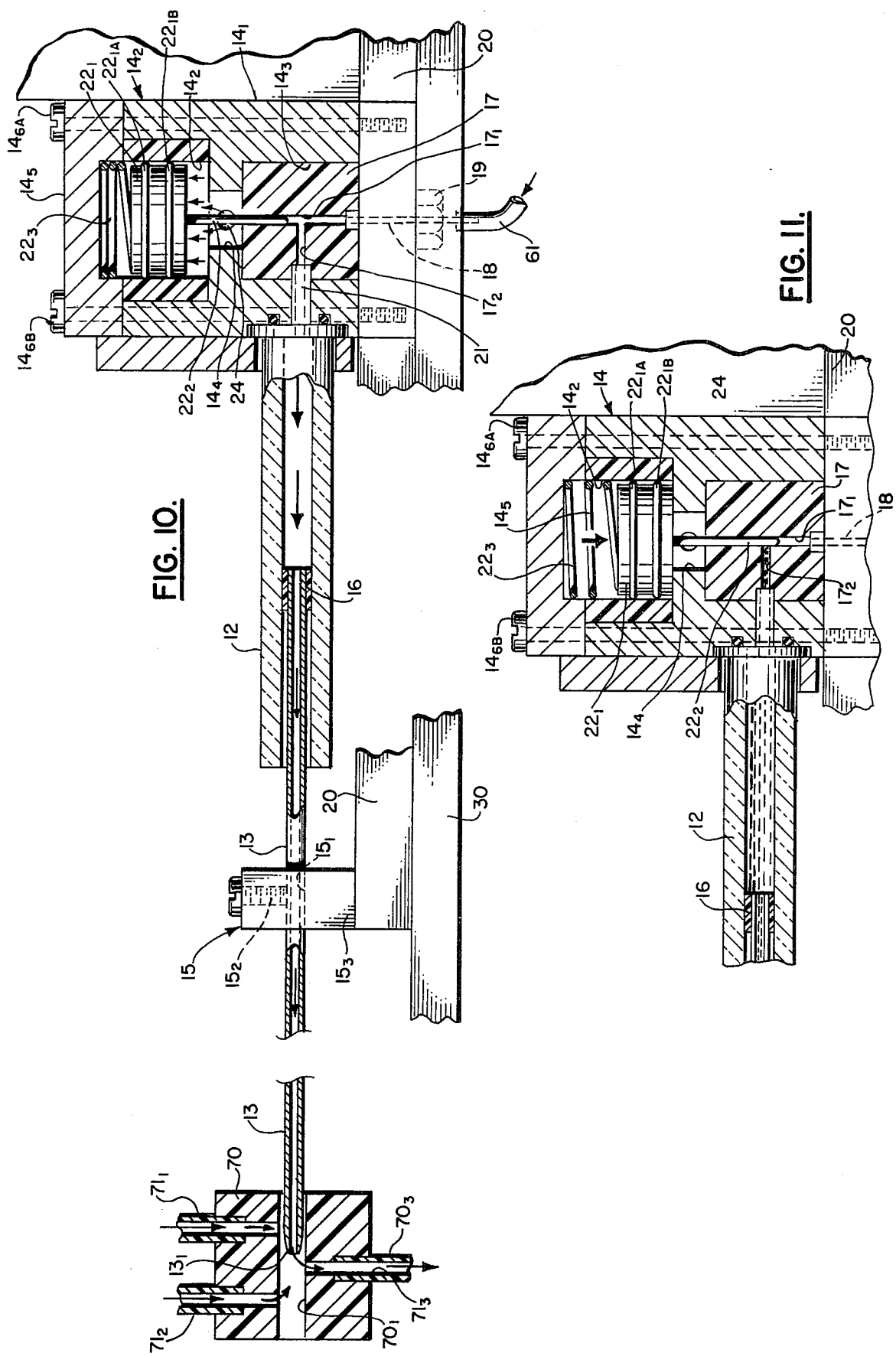

SEMI-AUTOMATIC AND AUTOMATIC FLUID INJECTORS

The present invention relates generally to fluid injectors, or apparatus, for measuring and injecting accurately measured quantities of fluids in a semi-automatic or full automatic mode. It relates particularly to the use of such devices for the measurement and injection of very small, accurately measured quantities of gas and liquid specimens into various media, e.g., modern analytical instruments such as mass spectrographs or gas chromatographs.

Fluid injection devices, particularly needle syringes, have gained wide acceptance by industry, universities, and by the scientific community, generally, for use in dispensing infinitesimally small, accurately measured fluid specimens, e.g., to modern analytical instruments such as mass spectrometers and gas chromatographs. Such syringes embody apparatus comprising a tubular body or barrel, on the forward end of which is fitted a hollow or tubular needle and, at the opposite end, a slidable plunger which travels within the bore of the barrel. Devices of such character are capable of dispensing very small fluid specimens, accurately measured, on the order of a few microliters, or very small fractions of a microliter, e.g., from about 0.01 to about 5 microliters, or fractional parts thereof.

An automated fluid injection device which has proven admirably capable of such usage is that described by pending Application Ser. No. 749,804 filed Dec. 13, 1976, the disclosure of which is herewith incorporated by reference. The automatic fluid injector disclosed in this Application represents a major advancement in the art in that, inter alia, the conventional plunger normally associated with the syringe barrel has been eliminated, and the barrel at one end of which is yet fitted the standard needle, or cannula, is fitted at its other end with an on-off valve, and the barrel is slidable relative to the needle so that on opening of the valve the instrument can be cleaned and purged, and then, on closure of the valve, filled with an accurately measured amount of a fluid specimen which can then be injected by movement of the barrel relative to the needle. The needle, in effect, moves rearwardly into the barrel to displace and eject the fluid specimen through the dispensing end of the needle, the amount of fluid specimen to be injected being predetermined by the preset volume to be displaced from the barrel by the extent of its forward movement which moves the rearward end of the needle into the barrel.

While, as suggested, the instrument described in said Application has been admirably successful, further improvements are nonetheless desired.

It is accordingly a primary object of the present invention to provide novel fluid injectors readily adaptable to perform the basic cyclic functions of purging and cleaning, filling, and injecting fluid specimens, in semi-automatic and full automatic modes of operation, as desired.

A particular object is to provide apparatus capable of withdrawing precisely measured, infinitesimally small quantities of gas or liquid specimens from prefilled vials or containers, injecting the specimens in seriatim in reproducible quantities, and cleaning prior to subsequent withdrawal and injection of subsequent specimens.

A further object is to provide apparatus of simple, inexpensive and compact construction, particularly apparatus which can be readily serviced and operated, which apparatus readily lends itself to rapid mass production techniques.

Yet another object is to provide apparatus embodying further improvements over those devices specifically disclosed and claimed in U.S. Pat. Nos. 3,754,443; 3,824,859; 3,885,438; 3,940,995; and 4,000,654.

These and other objects are achieved in accordance with the present invention which embodies improvements in fluid injector devices, notably semiautomatic and automatic fluid injector systems, constituted of (a) a fluid injector sub-assembly, (b) an injector feed unit, inclusive of a fixed probe assembly, and (c) a magazine, or feed supply chamber, for delivery of a fluid specimen containing vial to the probe assembly for penetration and pick-up of fluid specimen therefrom by the probe of said assembly for delivery to said fluid injector sub-assembly.

(a) The fluid injector sub-assembly is comprised of a barrel, or hollow tubular member, a hollow needle or cannula slidably mounted within the forward end of said barrel, and a valve located at the rearward end of said barrel for opening and closing the barrel to the flow of a fluid specimen therethrough from a suitable source. The needle, barrel and valve are all mounted upon a plate slidably affixed to a base plate. The needle is rigidly affixed to the slidable plate, and the relative motion between the barrel and needle produces ejection of an accurately measured portion of a fluid specimen, such action being provided by suitable drive means. Preferably, the valve is physically integrated with the rearward end of the barrel and provided with a stem which is actuatable and movable, suitably by a piston unit, to open and close the valve to the flow of fluid specimen, and both the barrel (which is moved relative to the needle) and valve are actuated and moved by a different drive means. Suitably, a second piston unit provides the relative movement between the barrel and needle required in the injection of a fluid specimen, and a third drive means, suitably a piston unit, reciprocates the slide plate relative to the base plate to move the fluid injector along a predetermined path for insertion of the dispensing end of the needle into, e.g., a septum inlet of an analytical instrument.

(b) The injector feed sub-assembly is comprised of a hollow probe, or pair of hollow probes, affixed to said slide plate. In one aspect, a single hollow probe with upper and lower openings providing a single conduit can be employed such that in a first cycle of a timed sequence means are employed which pressurize the fluid contents of a vial after penetration by the probe of a vial transported thereto by the magazine, or supply chamber, the probe acting in a second cycle of a timed sequence as a conduit for conveying the fluid contents of the vial to the barrel of the fluid injector sub-assembly. Preferably, a pair of hollow probes are employed, and these can be parallelly or concentrically mounted, preferably the latter. One probe of the pair, in this instance, is generally employed to pressurize the contents of a vial, while the other serves as a conduit for the transport of a fluid specimen from a vial delivered by the magazine or feed tray to the fluid injector sub-assembly. In either instance, means are thus provided which pressurize the fluid contents of a vial after its penetration by one, or the pair of probes into the vial, and the fluid contents therefrom are conveyed via a conduit to the barrel of the fluid injector subassembly.

The probe assembly of said injector feed unit is affixed upon said slide plate, with the pointed end of the probe assembly facing upwardly for penetration of a septum of a downwardly faced vial brought thereto by the magazine, or feed supply chamber, the vial being transported and forced downwardly upon said probe such that the latter is caused to penetrate the septum of the vial for withdrawal of a fluid specimen therefrom.

In all aspects, the fixed probe assembly thus comprises a gas supply conduit with gas inlet and gas outlet means, a fluid specimen supply conduit with fluid specimen inlet means, and outlet means connected to the barrel of said fluid injector sub-assembly, and means for puncturing the septum of a fluid specimen containing vial. In its preferred aspects, the gas supply and fluid specimen supply conduits are mounted concentrically one member with respect to the other, the outer member of the pair being shaped in the form of a needle, the apex or pointed end being faced upwardly to serve as a means for puncturing the septum of a vial forced downwardly and impaled thereupon.

(c) The magazine sub-assembly, or supply chamber sub-assembly, is comprised of carrier means, or means adapted to carry a fluid specimen containing vial in an inverted position with its septum side faced downwardly in reciprocatable fashion such that on downward movement the septum portion of the vial can be impaled upon and pierced by the puncturing means of said fixed probe assembly such that the gas and fluid supply conduits lie within the vial, whereby the fluid contents of the vial can be pressurized by injection of gas into the vial via the gas inlet conduit and fluid specimen transported via the fluid specimen outlet to the barrel of the fluid injector sub-assembly. Suitably, the vial carrier means of the magazine, or supply chamber, is constituted of a reciprocable tubular member mounted within guide means, preferably a small diameter inner tubular member concentrically mounted within a large diameter outer tubular member which serves as guide means. The large diameter outer tubular member is retained in fixed position, while the small diameter inner tubular member is retained in a reciprocable position above the pointed end of the fixed probe. An inverted fluid containing vial carried within the reciprocable inner tubular member with its septum side faced downwardly can, by the actuation of suitable drive means, e.g., a piston unit, be moved downwardly to the probe assembly for penetration and pick-up of fluid specimen from the vial by said probe assembly. After penetration of a vial, after it has been pushed downwardly upon the probe, the fluid contents of the vial are pressurized for transport of fluid to the fluid injector sub-assembly. On opening the valve of said fluid injector sub-assembly, the fluid specimen can be flowed through the barrel and needle to effectively clean these members and, on closure of the valve, a measured amount of the fluid specimen can be trapped inside the barrel and needle, and then on thrust of the dispensing end of the needle into a suitable media, e.g., the septum inlet to an analytical instrument, the fluid specimen can be injected by a relative forward movement of the barrel such that the needle moves rearwardly therewithin to displace and cause ejection of the fluid specimen through the dispensing end of the needle and into the inlet of the analytical instrument.

In its preferred aspects, the instrument is adapted for repetitively and automatically carrying out the functions of cleaning, purging and filling the barrel and needle of the fluid injector sub-assembly with predetermined quantities of fluid specimens, in timed sequence, and the several sub-assemblies of the automatic fluid injector are generally contained within a housing, or housings.

The characteristics of a preferred automatic, or more preferably a semi-automatic fluid injector, and its principle of operation, will be more fully understood by reference to the following detailed description, and to the attached drawings to which reference is made in the subsequent description. Similar numbers are used in the different figures to represent similar parts or components, and subscripts are used with numbers where there is a plurality of similar components. Reference by use of a whole number to a component represented by a number characterized in the description as having a plurality of similar components is intended in a generic sense.

Figure 6:
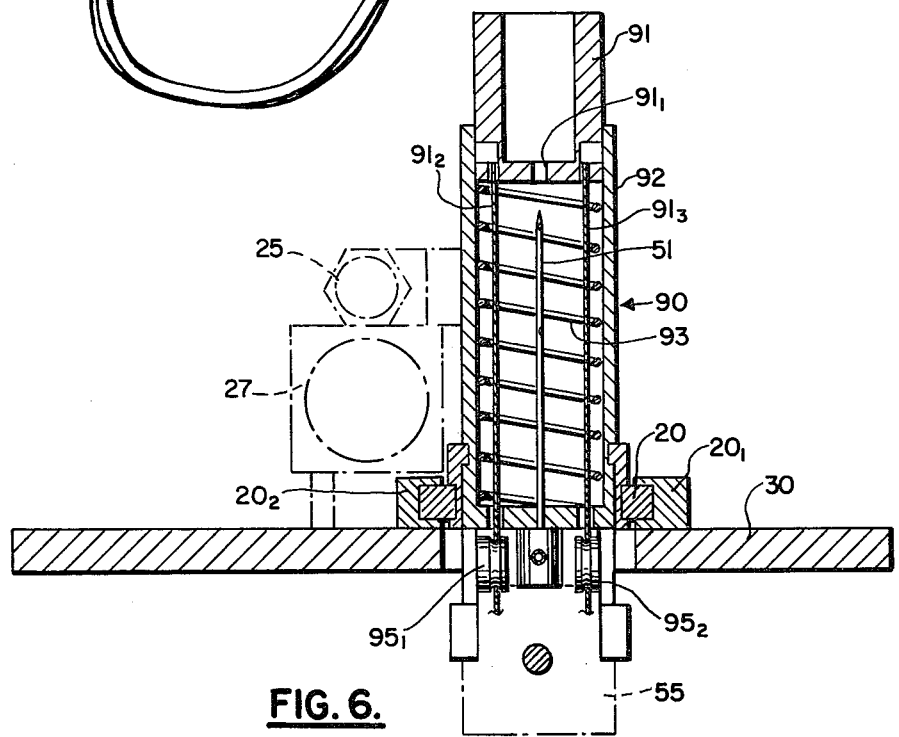
FIG. 6 depicts in some detail the injector feed unit, inclusive of its probe assembly as used for withdrawal of a fluid specimen from a vial, the vial being contained in a magazine, or supply chamber, of a semi-automatic type wherein the fluid containing vials are individually loaded by an operator.

FIG. 7, taken in connection with FIG. 6, further depicts in some detail the preferred probe assembly as used in the pick-up of a fluid specimen from a vial carried by the magazine, or supply chamber, for conveyance and delivery to the fluid injector sub-assembly.

Figure 8:
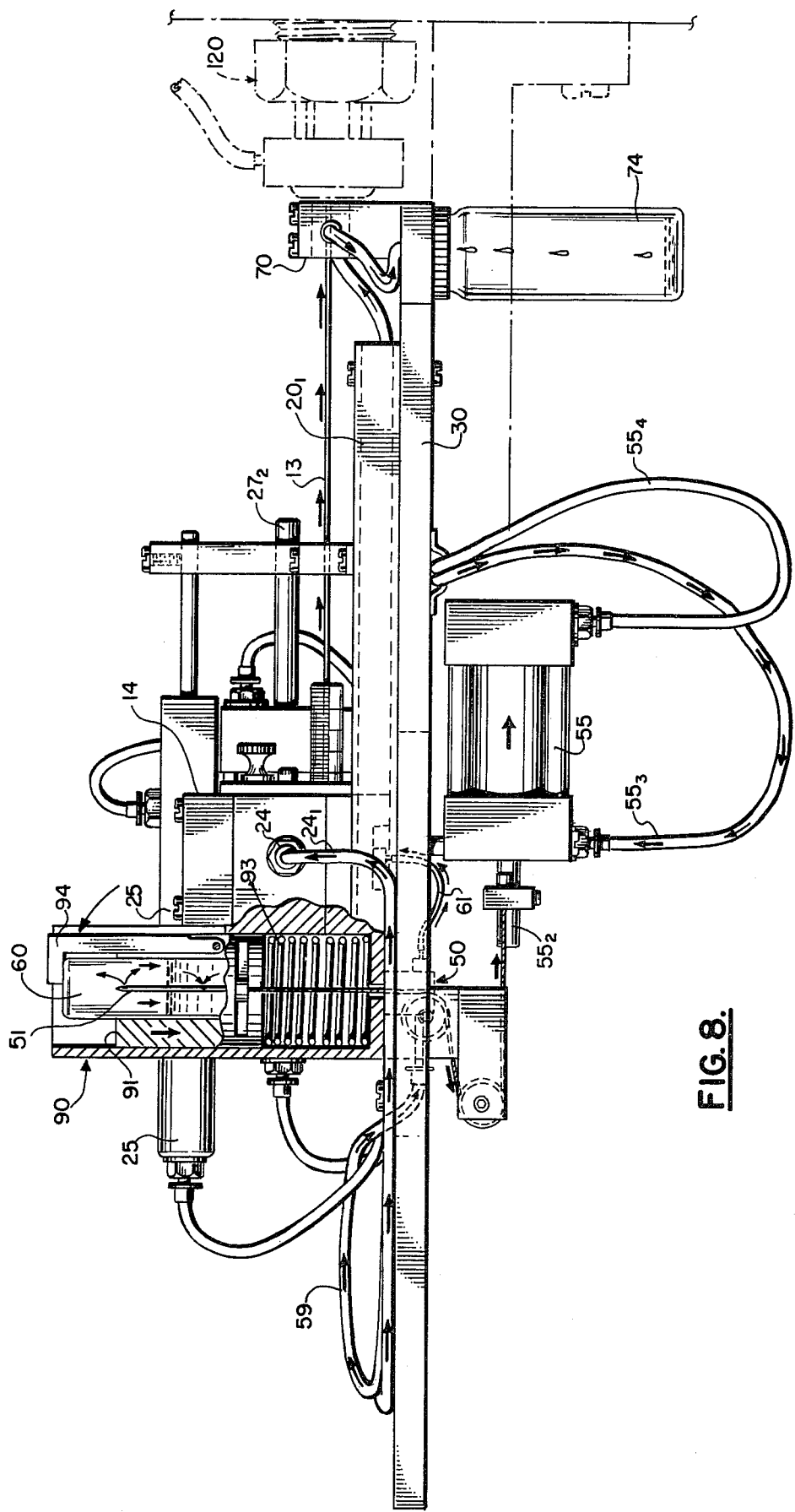

FIG. 8 depicts the principle components of the injector feed unit, inclusive of the probe assembly in its function of taking a fluid specimen from a filled vial delivered thereto by the magazine, or feed supply chamber, and the operation and function of these components in delivery of the fluid to the fluid injector sub-assembly for cleaning, purging and filling the fluid injector with a fluid specimen for subsequent injection.

FIG. 9 depicts, in specific detail, a preferred type of probe assembly for use in the withdrawal of a fluid specimen from a vial which is located in the magazine, or supply chamber, above said probe assembly.

FIGS. 10 and 11 depict a preferred type of fluid injector subassembly and its function in the withdrawal of a portion of a fluid specimen for purging, or cleaning, said unit, and its operation in withdrawing and injecting a fluid specimen.

Figure 12:
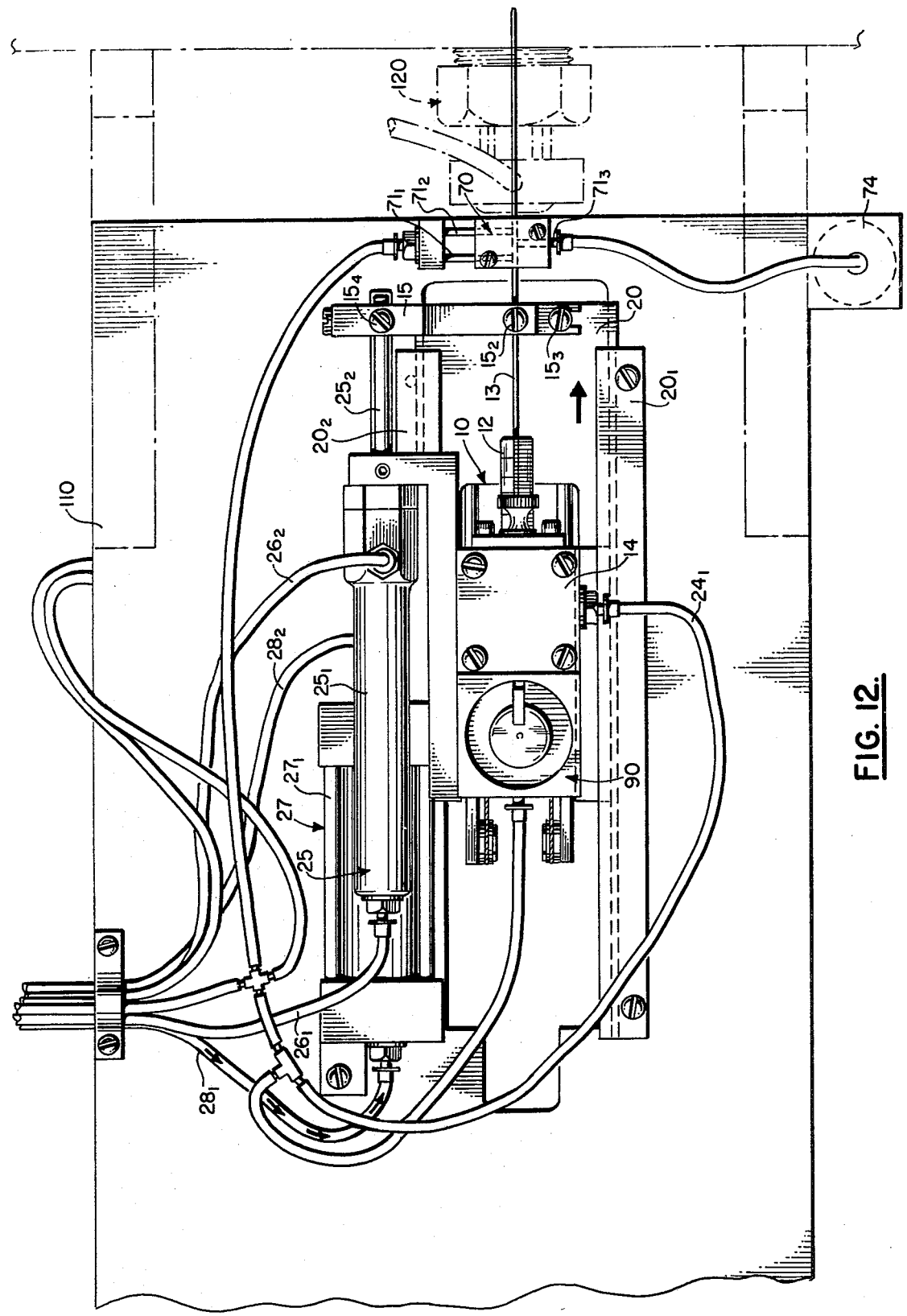
Figure 13:
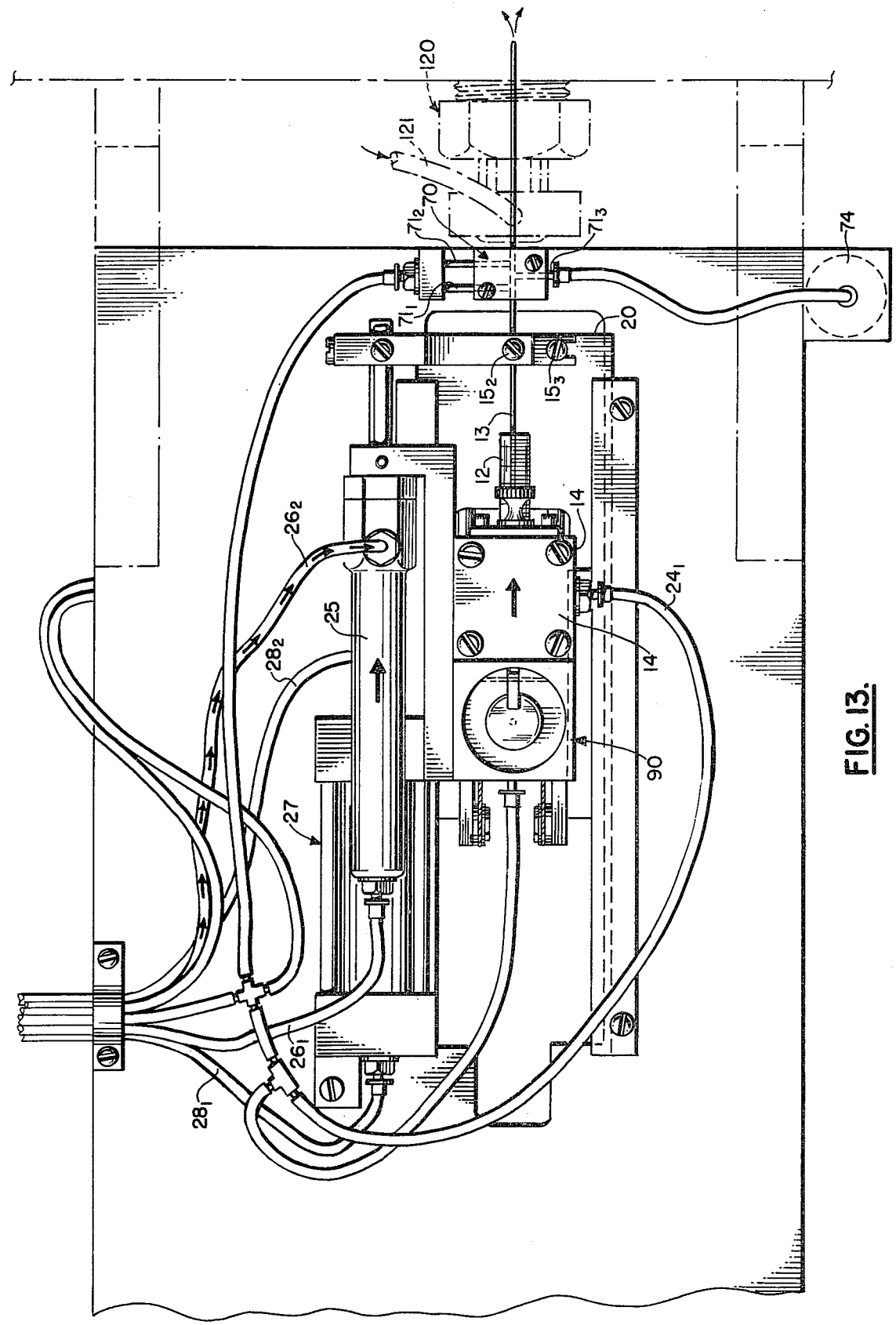

FIGS. 12 and 13, taken together with FIGS. 6–11, illustrate the overall functions employed in the process of withdrawing a fluid specimen from a vial, purging and cleaning, withdrawing and injecting a fluid specimen.

Referring generally to FIGS. 1 through 4, there is depicted a preferred type of semi-automatic fluid injector 100. The principle components of the semi-automatic fluid injector 100 include (a) a fluid injector sub-assembly 10, inclusive of a fluid injector per se, comprised of a barrel 12, hollow needle or cannula 13, drive means for reciprocation of one of these members relative to the other, and valve 14, (b) an injector feed assembly 50, inclusive of a fixed probe assembly 51 which constitutes the primary contact device of this sub-assembly used for the receipt of a fluid specimen, from (c) a magazine, or supply chamber 90, within which vials of fluid specimens are placed, in sequence, by an operator for pick-up by probe asembly 51 of injector feed assembly 50 for delivery to the barrel 12 of the fluid injector sub-assembly 10. After the purging and cleaning of the fluid injector sub-assembly 10 with a small initial portion of the fluid, an accurately measured portion of the fluid specimen can be injected into, e.g., an inlet 120 of an analytical instrument, via the direct action of the fluid injector, or fluid injector sub-assembly 10. These several sub-assemblies (a), (b) and (c) of the semi-automatic fluid injector 100, with other components, are generally contained in whole or in part within a casing, or housing 110, and responsive to automatic control means such as described in U.S. Pat. No. 3,754,443, supra.

The principal features and overall function of these several subassemblies and their relation one to another are described in further detail as follows:

(a) The fluid injector sub-assembly 10, the principal purpose of which is to accurately measure out a preselected quantity of a fluid specimen for delivery to a media, or instrument, includes generally a fluid injector per se which is comprised of a tubular component or barrel 12, a cannula or hollow needle 13 slidably mounted within the front end of said barrel, and a valve 14. In its more preferred aspects these several components of the fluid injector, i.e., barrel 12, needle 13 and valve 14, are mounted upon a movable plate 20, or plate which, in turn, is slidably mounted upon a base plate 30 affixed to a portion of the casing or housing 110. Suitably, and preferably, the movable plate 20 is mounted within a pair of channel members $20_1, 20_2$ affixed to base plate 30, which serve as a guideway or track within which plate 20 is moved, or reciprocated, e.g., via means of piston unit 25. It is essential that the barrel 12 and needle 13 be mounted such that one member can be reciprocably moved via appropriate drive means one member relative to the other, suitably while one member is fixed. Suitably, the needle 13 (FIG. 10) is rigidly secured to the slide plate 20 via the yoke 15, which contains therein a tubular section $15_1$ inclusive of an internal tubular gland through which the needle 13 is passed and retained in place by a set screw $15_2$, the tubular section being affixed upon slide plate 20 via set screws $15_3, 15_4$. So affixed, the needle 13 is not capable of movement relative to slide plate 20, but free relative movement of barrel 12 upon the slide plate 20 is permitted and such movement is accomplished via actuation of piston unit 25. Suitably, the rearward end of the needle 13 is provided with a tubular, or circumferential seal 16 affixed thereon, to prevent leakage of fluid around the annulus between the barrel 12 and the needle 13 as barrel 12 is moved thereupon.

The valve 14, best illustrated in FIGS. 10, 11, is located at the rearward end of barrel 12, its function being to open and close the barrel 12 to the flow of a fluid specimen delivered thereto. When the valve 14 is open, ingress of a fluid specimen through the barrel 12 and needle 13, and its egress therefrom, are permitted. When valve 14 is closed the flow is interrupted, and on closure to interrupt a previously flowing stream of a fluid specimen (as in purging and cleaning), a sample of the fluid specimen in measured volume is trapped within the barrel 12 and needle 13, and ready for subsequent ejection through the dispensing end $13_1$ of the needle.

Virtually any valve which can be controlled in response to a signal, particularly an electrical signal, to provide an on and off position can be employed. Suitably, the valve employed is an electrically controlled fluid actuated valve 14, e.g., a single acting fluid actuatable piston unit. Referring for convenience to FIGS. 10 and 11, the valve 14 is comprised of a body, or block $14_1$, which is provided with a pair of tubular openings $14_2, 14_3$ communicated one with the other via a central channel $14_4$. The tubular opening $14_3$ is provided with a tubular packing 17, the axial opening $17_1$ of which is communicated with the passageway formed within the tubular packing, generally comprised of a tubular segment 18 inserted therein, and held in place via an appropriate lock nut 19. A lateral opening $17_2$ which enters into the axial opening $17_1$ of packing 17 is connected with a tubular segment 21 which enters into the rear of barrel 12. The tubular opening $14_2$ is closed at the top by a plate $14_5$ by screws $14_{6A}, 14_{6B}, 14_{6C}$ and $14_{6D}$ which secures said top to the valve body $14_1$, and holds the valve 14 in place on the slide plate 20. A piston 22, inclusive of a head $22_1$ and stem $22_2$ provides the closure element for the valve. The head $22_1$, with its circumferential O-rings $22_{1A}, 22_{1B}$ is snugly fitted within the tubular opening $14_2$, the stem $22_2$ extending into the communicating channel or opening $14_4$ and entering partially into the axial opening $17_1$ of tubular packing 17. The head $22_1$ of the piston is biased in closed position (FIG. 11) by a spiral spring $22_3$ which is seated between the inner face of valve top plate $14_5$ and the outer face of head $22_1$ of the piston 22.

The functioning of valve 14 will be quite clear by continued reference to FIGS. 10 and 11. With reference to FIG. 10, on entry of a pressurized gas, e.g., air or nitrogen, into the valve body via opening 24, located within channel $14_4$, the downward force exerted by the helical spring $22_3$ is overcome and the valve is opened by withdrawal of the stem $22_2$ from the junction between openings $17_1, 17_2$ and a fluid specimen can enter through these openings to flow into and fill the barrel 12 and needle 13. Conversely, when no pressurized gas is admitted through the opening 24, the force of helical spring $22_3$ causes extension of stem $22_2$ into the junction formed by openings $17_1, 17_2$, thus closing off the flow of fluid specimen into the barrel 12 and needle 13 (FIG. 11).

The fluid injector sub-assembly 10 also includes means for actuating and reciprocating the barrel 12, suitably drive means which can be actuated and controlled in response to a signal, especially an electrical signal. Such means can be, as suggested, a piston unit, particularly a fluid actuatable piston unit 25 mounted alongside valve 14, both of which are carried upon slide plate 20. The piston unit 25, as shown, e.g., in FIGS. 12 and 13, is comprised of an outer cylinder $25_1$ with its piston, inclusive of rod $25_2$ and fixed head (not shown). The piston 25 is secured to the slide 20 via attachment through piston rod $25_2$ to an L-shaped bracket 35 which is secured to the side of valve 14 such that the piston unit 25 can be said to form an integral part of the fluid injector sub-assembly 10. Movement of barrel 12, relative to and without corresponding movement of the needle 13, can be produced by reciprocation of, inter alia, the valve 14 and barrel 12 without corresponding movement of slide 20. Such reciprocal movement is produced by alternate injections of a pressurized fluid, e.g., a gas such as air or nitrogen, via lines $26_1$ and $26_2$. The valve 14 and barrel 12 are moved forward (and fluid specimen injected) when pressurized gas is injected into the piston unit 25 via line $26_1$, and valve 14 and barrel 12 are moved rearwardly when pressurized gas is injected into the opposite side of piston unit 25 via line $26_2$.

A drive means for actuating and reciprocating the entire fluid injector sub-assembly 10, inclusive of slide 20 and its affixed components, is also required. In its preferred aspects, the slide plate 20 is slidably mounted upon the base plate 30 via means of guide ways $20_1, 20_2$ which are fitted along the longitudinal edges of a slot cut through the base plate 30, the slide plate 20 riding, being retained, and properly positioned within the guide ways $20_1, 20_2$. The slide plate 20 is also slotted, the valve 14 being retained and reciprocably movable within said slot by means of piston unit 25, as suggested. A fluid actuatable piston unit 27 is mounted on the lower side of piston unit 25, and upon base plate 30, and it is operatively associated with slide plate 20, its function being to reciprocate the entire slide plate 20 along a guided path for insertion, and withdrawal, of the dispensing end $13_1$ of needle 13 into a suitable media, e.g., a septum inlet 120 of an analytical instrument, into which a preselected accurately measured quantity of a fluid specimen is to be injected. Referring, e.g., to FIGS. 12 and 13, it will thus be observed that the piston unit 27 is comprised of a cylinder $27_1$ with its piston, inclusive of rod $27_2$ and head (not shown). The rod $27_2$ of piston unit 27 is attached via a suitable mounting bracket 15 to the slide 20 such that pressurized gas injected via line $29_1$ into the rearward end of said piston unit 27 causes movement of the slide plate 20 forward to thrust needle 13 into inlet 120 and, conversely, gas injected via line $29_2$ into the opposite, or forward, end of the piston unit 27 causes movement of the slide plate 20 in the opposite direction to withdraw needle 13 from inlet 120.

(b) The principle components of the injector feed assembly 50 are best shown by reference to FIGS. 2 and 6–9. These several components include generally a preferred type of probe assembly 51 which is mounted, or affixed, on the slide plate 20 with the pointed end of the probe portion per se faced upwardly into a magazine, or supply chamber 90, within which an inverted vial 60 (FIG. 7) containing a fluid specimen can be placed by an operator for pick-up, or receipt, by the probe of a portion of the fluid specimen therefrom, for delivery to the fluid injector sub-assembly 10. The septum portion of a vial 60 can be pierced by the pointed end of the probe on descent of the vial 60, produced by activation of the supply chamber 90 via the action of piston unit 55.

Referring, for convenience, first to FIG. 9, there is described a preferred type of probe assembly 51 for withdrawing a fluid specimen from a vial located within an overhead magazine, or supply chamber 90, within which the vial 60 is contained. The probe portion per se of probe assembly 51 is shown projected into a vial 60 which contains a fluid specimen which is held in place by a septum $60_1$, retained by a screw cover 60 located on top of said vial 60; which fluid is to be delivered to the fluid injector sub-assembly 10. The probe per se is, in effect, constituted of a pair of hollow needles $51_1, 51_2$ concentrically mounted, an inner needle $51_2$ contained within a larger diameter outer needle $51_1$. An axial opening, or passageway through the inner needle $51_2$ provides an internal conduit within which a pressurized gas, e.g., air or nitrogen, can be transmitted through an inlet to which is provided a connecting tube 59, the gas entering the upwardly oriented end of vial 60 via the opening or exit port $51_3$. Since the gas cannot escape the fluid contents of the vial are pressurized by the entering gas, the gases exerting a downward pressure. This pressure forces the fluid specimen into the lower entry port $51_4$, the fluid specimen descending through the annulus located between the inside wall of outer needle $51_1$ and the external wall of needle $51_2$, the fluid exiting via an outlet to the connecting tubing 61.

(c) The magazine, or supply chamber 90 is operated in close association with the probe assembly 51. The probe assembly 51, referring now for convenience to FIGS. 2 and 6–8, is mounted in fixed position on slide plate 20 with the pointed end of the needle extending upwardly into the magazine, or feed supply chamber 90. An upper small diameter inner tubular carrier member 91, within which a vial 60 can be placed (as shown in FIG. 7), is fitted concentrically within the opening of a guide member, suitably a larger diameter fixed tubular member 92, and is slidably movable upwardly and downwardly therein except to the extent that it is maintained in raised position by the presence of the helical spring 93 upon which it rests. In the position shown in FIG. 2, the spring 93 thus holds the carrier member 91, and consequently inverted vial 60 which rests therein, in a position wherein the latter is poised above the pointed end of the inverted probe 51. Downward movement of the carrier member 91, by means and in manner subsequently explained, will cause penetration of the septum $60_1$ of the vial 60 by the pointed end of the probe, and entry thereof into the vial 60 (as in FIG. 9), and simultaneously with the initiation of such downward movement a toe end $94_1$ of the pivoted L-shaped latch lock 94, which rides in a groove within the carrier member 91, will be rotated so that the small curved end $94_2$ of the lock 94 will move above, or in behind, the vial 60 and hold it securely in place while the pointed end of probe 51 is projected through the opening $91_1$ of carrier member 91 (FIG. 6) and then through the septum $60_1$ of vial 60, to penetrate same for pick-up and delivery of a fluid specimen to the feed injector sub-assembly 10.

By specific reference to FIG. 6 it will be observed that two parallel, alternately disposed guide lines $91_2, 91_3$ are affixed to the vial carrier member 91, these being extended through the fixed tubular member 92, and through ports in the bottom thereof, and that these lines are secured, after passage around pairs of parallelly aligned pulleys $95_1, 95_2, 96_1, 96_2$, to rod $55_2$ of piston unit 55, thus redirecting the direction of the force applied upon the carrier member 91 so that it can be reciprocated upwardly and downwardly by actuation of piston unit 55, to reciprocate piston rod $55_2$.

Figure 1:
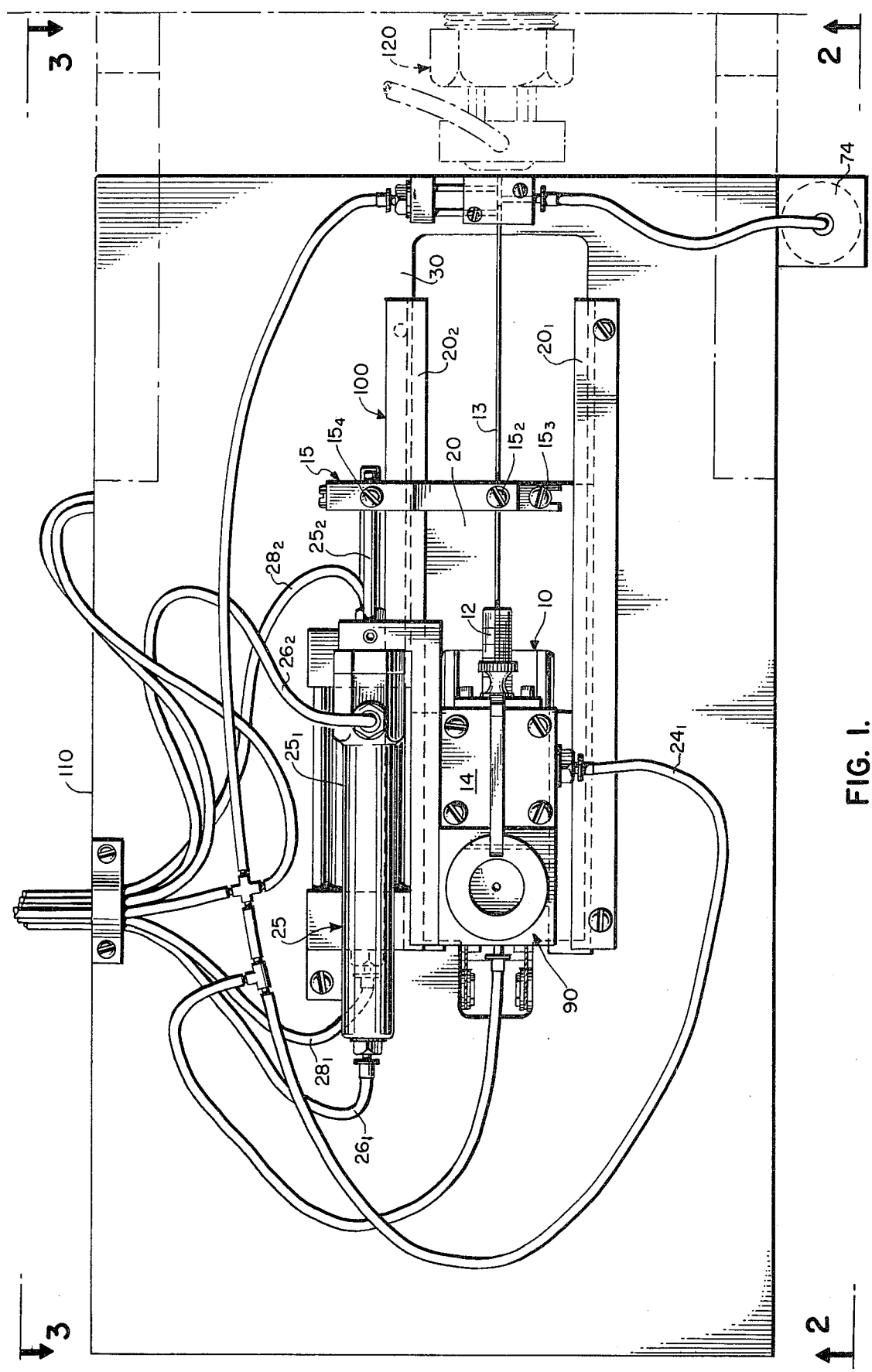
FIG. 1 depicts a plan view of a preferred semi-automatic fluid injector, inclusive of a portion of the housing, wherein is included (a) a fluid injector sub-assembly, (b) an injector feed unit, inclusive of its probe assembly, and (c) a magazine, or feed supply chamber.
Figure 2:
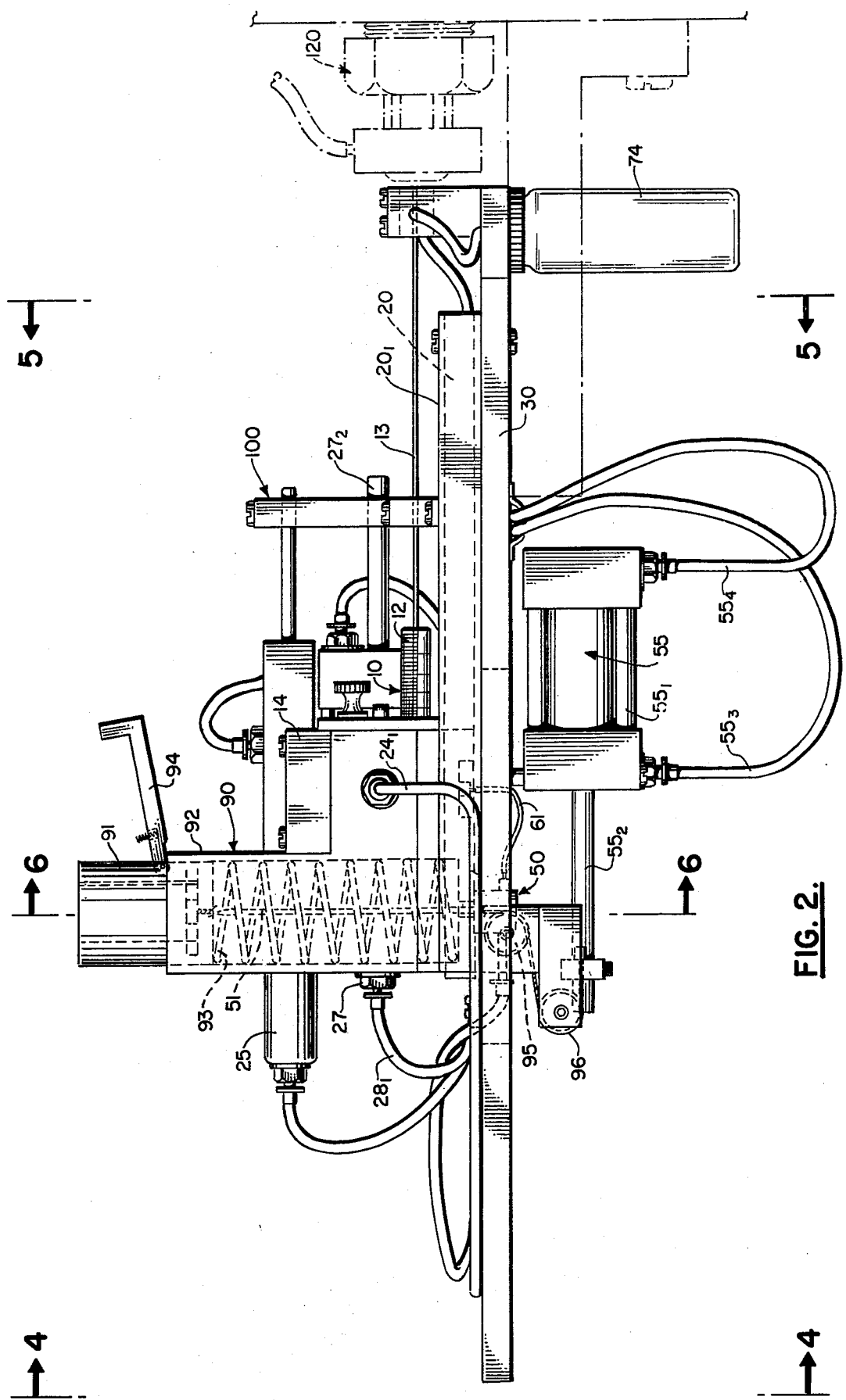
FIG. 2 depicts a right side elevation view of said semi-automatic fluid injector, the view being taken along line 2—2 of the preceding figure.
Figure 3:
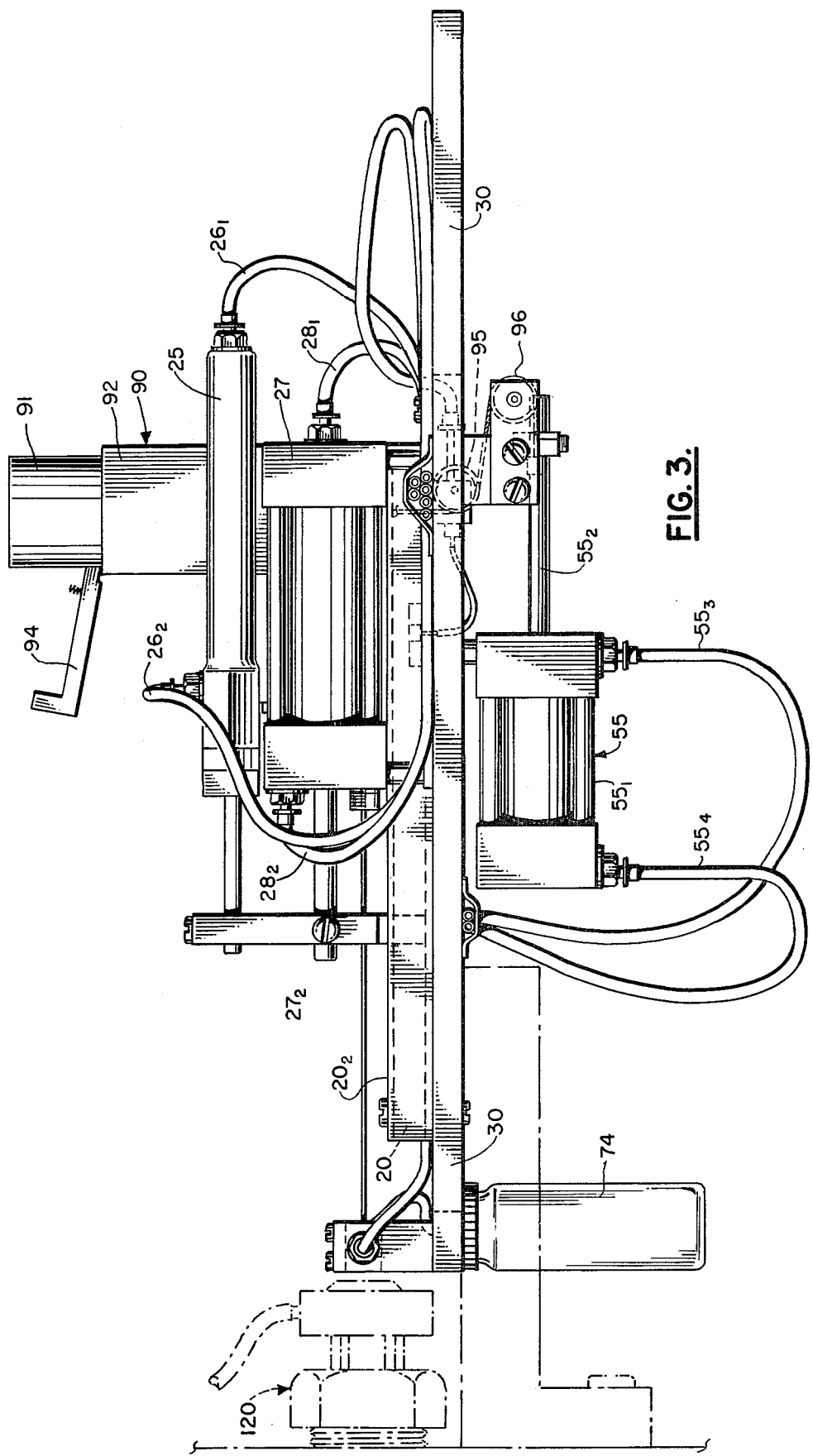
FIG. 3 depicts an opposite, or left, side elevation view of said semi-automatic fluid injector, the view being taken along line 3—3 of FIG. 1.
Figure 4:
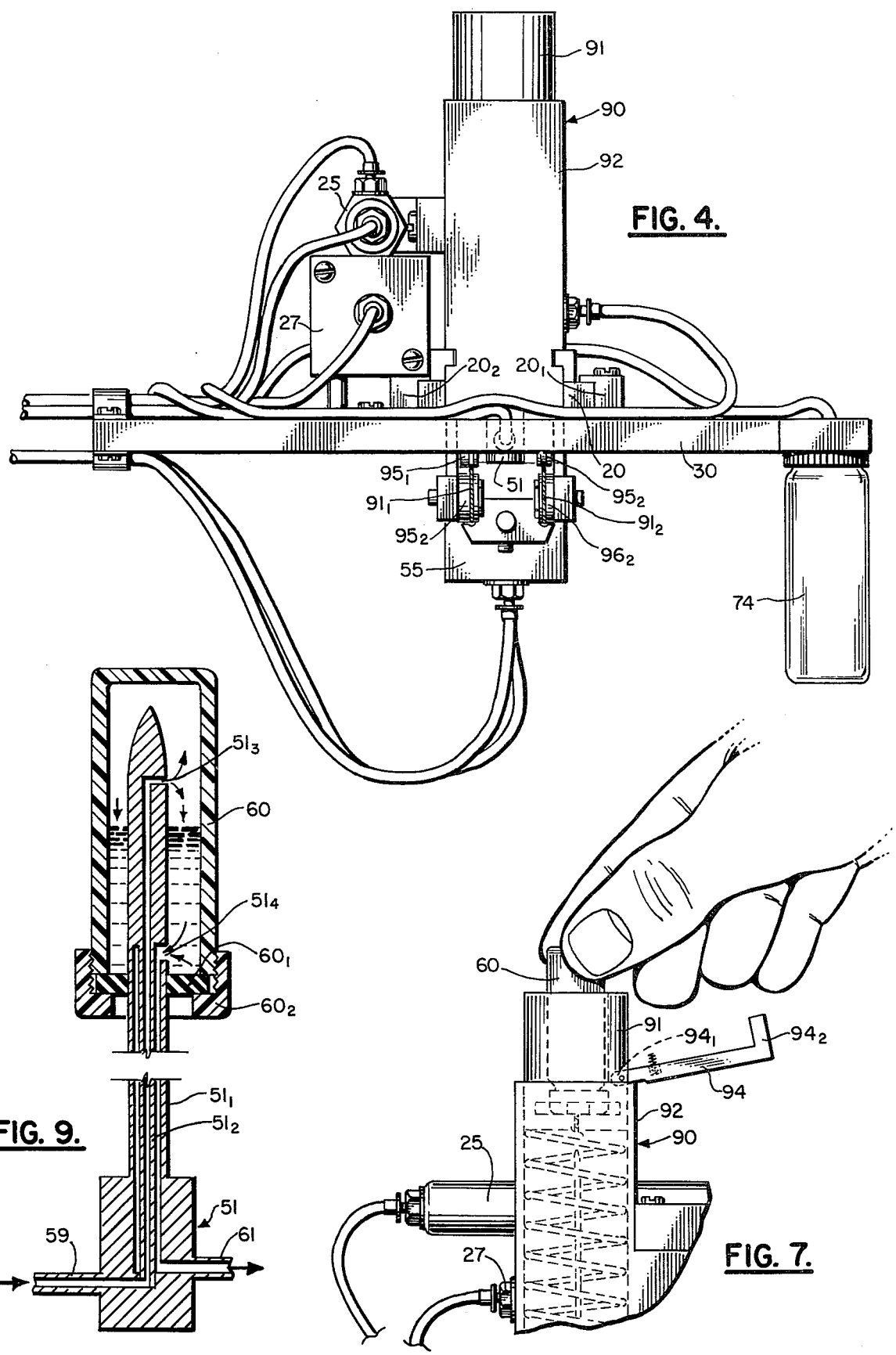
FIG. 4 depicts a rear side elevation view of said semi-automatic fluid injector, the view being taken along line 4—4 of FIG. 2.
Figure 5:
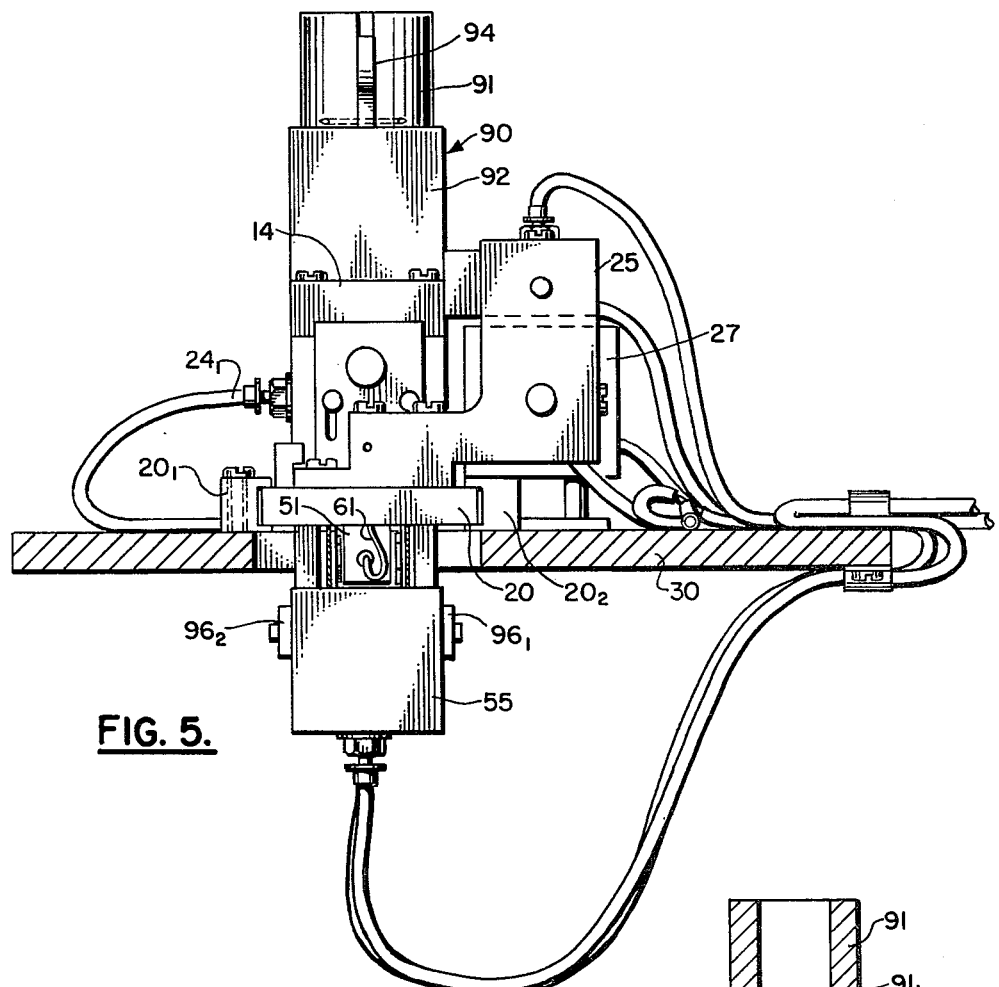
FIG. 5 depicts a side elevation view, in section, taken along line 5—5 of FIG. 2, illustrating in some further detail the semi-automatic fluid injector.

Referring, e.g., to FIGS. 2, 3 or 8, the double acting piston unit 55 is comprised of an outer cylinder $55_1$, with its included piston, inclusive of rod $55_2$ and head (not shown). The rod $55_2$ is reciprocated by alternate injection of a pressurized fluid, e.g., a gas such as air or nitrogen, into the cylinder $55_1$ via line $55_3$ to cause withdrawal of the piston rod $55_2$ (gas being simultaneously expelled via line $55_4$) to pull the carrier member 91 downwardly, or into cylinder $55_1$ via line $55_4$ to cause extension of the piston rod $55_2$ (gas being simultaneously expelled via line $55_3$) and permits the carrier member 91 to ascend, since it is biased in upward position by helical spring 93 of fixed tubular member 92. The probe assembly 51 and piston unit 55 are mounted in substantially the same vertical plane, this providing a mechanical advantage and favoring compactness of the unit.

An operating cycle is described by reference to the figures, particularly to FIGS. 5 through 13, these figures depicting a series of views describing the cleaning, purging, filling and injection of an accurately measured fluid specimen obtained from a vial delivered by the magazine, or feed supply chamber. The cycle can be repeated in timed sequence ad infinitum, as follows:

(a) Referring initially to FIG. 7, a vial 60, in inverted position, is loaded into magazine, or supply chamber 91 via an operator. On supplying a pressurized gas via inlet 24, as via line $24_1$, the valve 14 is opened (FIG. 10). On actuation of piston unit 55 the supply chamber 91, carrying the inverted vial 60, is carried downwardly and the septum $60_1$ of the vial 60 is penetrated by the pointed end of probe assembly 51 and fluid specimen taken from the vial as detailed with specific reference to FIG. 9. Gas injected via line 59 pressurizes the fluid contents of the vial 60 and delivers the fluid specimen via line 61 to barrel 12 of the fluid injector sub-assembly 10 via action of the injector feed unit 50, particularly characterized by the inverted probe assembly 51 which lies at the heart of said unit 50. First, the barrel 12 and needle 13 are purged and cleaned, this constituting the initial portion of an operating cycle.

Referring specifically to FIG. 8, a cleaning and purging action of the operating cycle is described. The injector feed sub-assembly 50, and magazine, or supply chamber 90, are activated by injection of pressurized gas via line $55_3$ into piston unit 55 causing inward thrust of piston rod $55_2$. In such action, the supply chamber 90, with inverted vial 60, is pulled downwardly, compressing spring 93, such that the septum of said vial 60 is penetrated by the pointed end of probe 51. Pressurized gas injected into probe 51 via line 59 enters the vial and forces fluid specimen therefrom via line 61, the fluid specimen entering the open valve 14, and rearward end of barrel 12 (FIG. 10) and flowing outwardly therefrom via the dispensing end $13_1$ of the needle 13.

The fluid specimen is thus passed through line 61, inlet 18 and openings $17_1, 17_2$ into the rear of barrel 12, the fluid passing through the rearward end of said barrel 12 and then through the bore of needle 13, the flowing stream of fluid cleaning and purging the barrel 12 and needle 13 of any contamination, e.g., may be present from a previous injection with a different fluid specimen.

Continuing for convenience to refer to FIG. 8, the dispensing end $13_1$ of needle 13 is located within a fluidic diversion valve 70. Referring for convenience to FIG. 10, a gas, e.g., air or nitrogen, is passed through the dual lateral openings $71_1, 71_2$ via line 72, and around the annulus within which the needle is contained to sweep fluid specimen from the needle 13 through outlet opening $71_3$. The excess liquid is conveyed via line 73 to flush bottle 74.

(b) The cleaning and purging step is interrupted, and the barrel 12 and needle 13 filled with a fluid specimen for delivery by closure of valve 14. To close the valve 14, and complete the cleaning and purging step of the sequence, as best shown by reference to FIG. 10, the flow of pressurized gas to the valve 14 via line $24_1$ and opening 24 is interrupted, this releasing the tension on helical spring $22_3$. As this occurs, the helical spring $22_3$ (formerly under tension as depicted in FIG. 10) urges the piston head $22_1$ downwardly, the piston rod $22_2$ being thrust past the junction of axial opening $17_1$ and lateral opening $17_2$ thus cutting off the flow of fluid specimen via line 61 into inlet 18, and openings $17_1, 17_2$ at the rearward end of barrel 12. In interrupting the flow in this manner, an uncontaminated portion of the fluid specimen is trapped within the barrel 12 and needle 13 of the fluid injector sub-assembly 10. The injection of a gas into the dual lateral openings $71_1, 71_2$, as begun in step (a), supra, is continued during the time, and thereafter, for a sufficient time to dry the needle 13.

(c) The purging, cleaning, filling and drying functions of injector feed assembly 50 now having been completed the supply chamber 90, with its partially or wholly exhausted vial 60 can, at this time, be withdrawn, raised or repositioned for charging a fresh vial, for use in a subsequent cycle. Withdrawal of the supply chamber 90 to its elevated position is accomplished by injection of pressurized gas via line $55_4$ into piston unit 55 (gas being expelled via line $55_3$). Such action, not specifically detailed, is readily apparent by reference to FIG. 8 which can be read with all of the black arrows reversed. In other words, piston rod $55_2$ in this instance is thrust outwardly, the relaxation of the downward thrust previously applied upon guidelines $91_2, 91_3$ permitting the supply chamber to ascend under the force applied by the decompression of helical spring 93 (FIG. 6); and probe 51 is disengaged from the vial 60. The latch 94, as this occurs, is pushed aside by the ascending supply chamber 91 and said vial can now be removed from the supply chamber 91 and replaced by a filled vial for use in the next cycle of operation (FIG. 7).

(d) Preparation for the injection of the fluid specimen now trapped in measured quantity in barrel 12 and needle 13 is best described, initially, by specific reference to FIG. 12. Pressurized gas, e.g., air or nitrogen, is now injected or passed via line $28_1$ into piston unit 27, this producing outward thrust of piston rod $27_2$ thus causing the forward movement of slide plate 20 within guideways $20_1, 20_2$. The dispensing end $13_1$ of needle 13 is thus thrust deeply in the septum inlet 120 of the analytical instrument, e.g., a gas chromatograph, and the stage is now set for the actual injection.

(e) The actual injection step is shown by reference to FIG. 13. Pressurized gas, e.g., air or nitrogen, is injected via line $26_2$ into the forward end of piston unit 25 wherein, because the piston rod $25_2$ is incapable of further forward movement, the entire piston unit 25, magazine or supply chamber 90, injector feed unit, inclusive of probe assembly 51, valve 14, and barrel 12, which are slidably mounted upon slide plate 20, are thrust further forward while the needle 12 remains in fixed position. Such action, in effect, causes the barrel 12 to move relative to the needle 13, such that the rearward end of the latter is, in effect, thrust inwardly into the barrel 12 to displace fluid specimen from the dispensing end 13₁ of the needle 13. As this occurs, the measured increment of the fluid specimen is injected into the septum inlet 120 and conveyed into the instrument via carrier gas introduced at line 121. The volume of fluid specimen actually injected is equal to the volume of fluid specimen displaced by the needle on its movement into the barrel 12.

(f) After injection of the fluid specimen, the slide 20 is then repositioned rearwardly, and needle 13 withdrawn from the septum inlet 120 by injection of pressurized gas via line 28₂ into the front end of piston unit 27 (while gas is expelled via line 28₁). [At this point in time magazine, or supply chamber 90 could be repositioned relative to the probe assembly 51, and a fresh vial delivered for pick-up in lieu of such step having been previously conducted as in step (c)].

(g) The barrel 12 of the fluid injector sub-assembly 10 is next repositioned in relation to needle 13, as just prior to initiation of step (e) wherein the barrel 12 was slid over the rear end of the needle 13 to eject the fluid specimen. This is accomplished by injecting pressurized gas via line 26₁ to cause reverse movement of piston unit 25, magazine or supply chamber 90 and barrel 12, while needle 13 is held in fixed relative position.

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the fluid injector is normally constructed of glass, but can be constructed of a plastic or plastic-like material. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or elastic-like materials, such as natural or synthetic rubbers, can also be employed.

The fluid injector sub-assembly (except for the barrel), the injector feed assembly, particularly the needle and probes, the piston units, and the like, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode or particular sequence of withdrawing or delivering fluids, can be made without departing the spirit and scope of the invention, as will be apparent to those skilled in this art.

Having described the invention, what is claimed is:

1. A fluid injector, or apparatus, for use in withdrawing a fluid specimen from a fluid specimen containing septum type vial, for accurately measuring, and then injecting in pre-selected quantity into a medium which, in combination, comprises (a) a fluid injector sub-assembly, inclusive of
a barrel,
a hollow needle mounted on an end of the barrel providing an opening from the dispensing end of said needle through said needle and barrel, and
means for opening said barrel to permit flow of fluid specimen through said barrel and needle, and closure to interrupt said flow, (b) an injector feed sub-assembly, inclusive of
a fixed probe assembly comprising
a gas supply conduit with gas inlet and gas outlet means,
a fluid specimen supply conduit with fluid specimen inlet means, and outlet means connected to the barrel and operatively associated with the means of said fluid injector sub-assembly which opens and closes said barrel to the flow of said fluid specimen, and
means for puncturing the septum of the fluid specimen containing vial so that the gas and fluid specimen supply conduits can enter into and lie within the vial, (c) a magazine sub-assembly, inclusive of
means adapted to carry a fluid specimen containing vial in an inverted position with its septum side faced downwardly, in reciprocatable fashion, such that on downward movement the septum portion of the vial can be impaled upon and pierced by the puncturing means of said fixed probe assembly such that the gas and fluid specimen supply conduits lie within the vial, the fluid contents of the vial can be pressurized by injection of gas into the vial via the gas inlet conduit and fluid specimen transported via the fluid specimen outlet to the barrel, whereby on the ingress of an initial portion of the fluid specimen the barrel and needle can be purged and cleaned, an accurately measured portion of the fluid specimen can then be trapped, and then injected on insertion of the dispensing end of the needle into said medium.

2. The apparatus of claim 1 wherein a valve constitutes the means associated with said fluid injector sub-assembly for opening and closing the barrel.

3. The apparatus of claim 2 wherein the valve is comprised of a piston unit, the rod portion of which effects the opening and closing of the valve.

4. The apparatus of claim 1 wherein the fixed probe assembly of the injector feed sub-assembly is comprised of a pair of concentric hollow needles, one of which serves as the gas supply conduit and the other of which serves as the fluid specimen supply conduit.

5. The apparatus of claim 4 wherein the inner member of the pair serves as the gas supply conduit and the outer member of the pair serves as the fluid specimen supply conduit.

6. The apparatus of claim 5 wherein the apex of the outer member is pointed, this constituting the means for puncturing the septum of a fluid specimen containing vial delivered thereto for withdrawal of a fluid specimen.

7. The apparatus of claim 1 wherein the magazine sub-assembly includes a pair of concentric tubular members, a large diameter outer tubular member within which is fitted an inner small diameter tubular member, the large diameter outer tubular member being fixed while the inner small diameter tubular member is movable upwardly and downwardly within said large diameter outer tubular member and adapted to carry the fluid specimen containing vial in inverted position with its septum side faced downwardly so that the septum can be pierced by the puncturing means of said fixed probe assembly on downward movement of said inner small diameter tubular member.

8. The apparatus of claim 7 wherein the inner small diameter member is spring biased in raised position within the outer large diameter member, and actuated by a piston unit.

9. The apparatus of claim 7 wherein a wall of the outer large diameter member is notched and carries an L-shaped latch oriented and pivotally secured at the lower end of the longest side of said latch so that the short side of the latch and toe portions are extendable inwardly, the inner small diameter member is grooved such that the toe portion of the L-shaped latch rides therein, such that downward movement of the inner small diameter member presses the toe of the L-shaped latch outwardly to cam the short side of the L-shaped latch inwardly to block and hold the vial in place as the septum thereof is pierced by the puncturing means of said fixed probe assembly.

10. The apparatus of claim 9 wherein the inner small diameter tubular member is biased in raised position by a helical spring seated between said inner and outer large diameter tubular members, and the inner small diameter tubular member is operatively associated with an actuating piston unit which produces reciprocating movement of said inner small diameter tubular member.

11. A fluid injector, or apparatus, for use in withdrawing a fluid specimen from a septum type vial, for accurately measuring, and then injecting, said fluid specimen in pre-selected quantity into a septum inlet of an analytical instrument which, in combination, comprises a fixed base plate, which can constitute a portion of a housing for said fluid injector,
a slide plate reciprocably, unidirectionally movable upon said base plate,
means for reciprocation of said slide plate, and sub-assemblies including
(a) a fluid injector sub-assembly, inclusive of
  a barrel,
  a hollow needle affixed to said slide plate, said needle being slidably mounted within an end of said barrel so that said barrel is movable relative to said needle, an opening being provided from the dispensing end of said needle through said needle and barrel,
  a valve for opening said barrel to permit ingress of a fluid specimen into said barrel and needle, and for closing said barrel to interrupt said flow of fluid specimen into said barrel and needle,
  means for moving said barrel relative to the needle on closure of said valve,
(b) an injector feed sub-assembly, inclusive of
  a probe assembly affixed upon said slide plate comprising
    a gas supply conduit with gas inlet and gas outlet means,
    a fluid specimen supply conduit with fluid specimen inlet means, and outlet means connected through the valve to the barrel of said fluid injector sub-assembly,
    puncture means for penetration of the septum of said vial, and passage therethrough of said gas and fluid specimen supply conduits which can enter into and lie within the vial,
(c) a magazine sub-assembly, affixed upon said slide plate directly above the probe assembly of said injector feed subassembly, inclusive of
  a pair of members, a fixed member which serves as a guide for a tubular member movable upwardly and downwardly relative to said fixed member, adapted to carry a fluid specimen containing vial in inverted position with its septum side faced downwardly such that on downward movement of said tubular member the septum portion of said vial can be impaled upon and pierced by the puncture means of said probe assembly such that the gas supply and fluid specimen supply conduits lie within the vial, whereby, on opening the valve of the fluid injector sub-assembly, the fluid contents of the vial can be pressurized by injection of gas into the vial via the gas inlet conduit and fluid specimen transported via the fluid specimen outlet through the valve to clean and purge the barrel and needle, the valve can then be closed to trap an accurately measured volume of the fluid specimen within the barrel and needle, the slide plate can then be moved forward by actuation of said means for reciprocation of said slide plate to insert the dispensing end of the needle into the septum inlet of said analytical instrument, and the measured quantity of fluid specimen then injected by actuation of said means which moves the barrel forward relative to the needle such that entry of the latter into the barrel displaces fluid specimen which is injected via the dispensing end of the needle into the septum inlet of the analytical instrument.

12. The apparatus of claim 11 wherein a fluidic diversion valve is mounted on the base plate, said fluidic diversion valve comprising a tubular member the axial opening of which is aligned upon the septum inlet of said analytical instrument and adapted for receipt and movement therethrough of the needle of said fluid injector sub-assembly, and a lateral passageway intersecting with said axial opening for carrying away waste fluid specimen ejected from the dispensing end of the needle during a purging and cleaning step, and through which a gas can be injected to dry the dispensing end of the needle prior to insertion of the needle into the septum inlet of an analytical instrument for an injection.

13. The apparatus of claim 11 wherein the valve of said fluid injector sub-assembly is comprised of a piston unit, the rod portion of which effects the opening and closing of the valve.

14. The apparatus of claim 11 wherein the fixed probe assembly of the injector feed sub-assembly is comprised of a pair of concentric hollow needles, one of which serves as the gas supply conduit and the other of which serves as the fluid specimen supply conduit.

15. The apparatus of claim 14 wherein the inner member of the pair serves as the gas supply conduit and the outer member of the pair serves as the fluid specimen supply conduit.

16. The apparatus of claim 15 wherein the apex of the outer member is pointed, this constituting the means for puncturing the septum of a fluid specimen containing vial delivered thereto for withdrawal of a fluid specimen.

17. The apparatus of claim 11 wherein the magazine sub-assembly includes a pair of concentric tubular members, a large diameter outer tubular member within which is fitted an inner small diameter tubular member, the large diameter outer tubular member being fixed while the inner small diameter tubular member is movable upwardly and downwardly within said large diameter outer tubular member and adapted to carry the fluid specimen containing vial in inverted position with its septum side faced downwardly so that the septum can be pierced by the puncturing means of said fixed probe assembly on downward movement of said inner small diameter tubular member.

18. The apparatus of claim 17 wherein the inner small diameter member is spring biased in raised position within the outer large diameter member, and actuated by a piston unit.

19. The apparatus of claim 17 wherein a wall of the outer large diameter member is notched and carries an L-shaped latch oriented and pivotally secured at the lower end of the longest side of said latch so that the short side of the latch and toe portions are extendable inwardly, the inner small diameter member is grooved such that the toe portion of the L-shaped latch rides therein, such that downward movement of the inner small diameter member presses the toe of the L-shaped latch outwardly to cam the short side of the L-shaped latch inwardly to block and hold the vial in place as the septum thereof is pierced by the puncturing means of said fixed probe assembly.

20. The apparatus of claim 19 wherein the inner small diameter tubular member is biased in raised position by a helical spring seated between said inner and outer large diameter tubular members, and the inner small diameter tubular member is operatively associated with an actuating piston unit which produces reciprocating movement of said inner small diameter tubular member.

21. A fluid injector, or apparatus, for use in withdrawing a fluid specimen from a septum type vial, for accurately measuring, and then injecting said fluid specimen in pre-selected quantity into a septum inlet of an analytical instrument which, in combination, comprises
a fixed horizontally oriented base plate which can constitute a portion of a housing for said fluid injector,
a fluidic diversion valve mounted on the forward end of said base plate, said fluidic diversion valve comprising a tubular member the axial opening of which is aligned upon the septum inlet of said analytical instrument, and a lateral passageway intersecting with said axial opening,
a slide plate reciprocably, unidirectionally movable upon said base plate,
a first piston unit mounted upon said base plate, the rod portion of which is affixed to said slide for actuation and reciprocation thereof, and
sub-assemblies including
(a) a fluid injector sub-assembly inclusive of
a barrel,
a hollow needle affixed upon said slide plate, said needle being slidably mounted within the forward end of said barrel so that said barrel is movable relative to said needle, an opening being provided from the dispensing end of said needle through said needle and barrel, said needle being coaxially aligned with and extendable into the axial opening through said fluidic diversion valve, into the area of the lateral passageway which intersects with said axial opening, and into the septum inlet of the septum inlet of the analytical instrument on extended forward movement of said slide plate,
an on-off valve for opening and closing the rearward end of said barrel to the flow of a fluid specimen, and
a second piston unit mounted on said slide plate for moving said barrel relative to said needle on closure of said on-off valve,
(b) an injector feed sub-assembly, inclusive of
a probe assembly affixed to said slide plate comprising a pair of concentric hollow conduits, one of which serves as a gas supply conduit inclusive of a gas inlet and gas outlet, and the other of which serves as the fluid specimen supply conduit inclusive of a fluid specimen inlet, and a fluid specimen outlet which is operatively connected through the on-off valve to the rearward end of the barrel of said fluid injector sub-assembly, the outer conduit being shaped in the form of a needle with the pointed end faced upwardly to provide means for puncturing a septum of a septum type fluid specimen containing vial transported thereto for extension of said probe assembly into the interior of said vial, and
(c) a magazine sub-assembly inclusive of
a pair of concentric tubular members, a large diameter outer tubular member affixed upon said slide plate directly above said probe assembly which serves as a guide for an inner small diameter tubular member fitted therein, the inner small tubular member being biased in upward position by a helical spring seated between said pair of tubular members, but being movable upwardly and downwardly within said large diameter outer tubular member and adapted to carry a fluid specimen containing vial in inverted position with its septum side faced downwardly so that the septum can be pierced by the upwardly faced pointed end of the probe assembly on the descent of said inner small diameter tubular member,
whereby, on opening the valve of the fluid injector sub-assembly, the fluid specimen contents of the vial can be pressurized by injection of gas into the vial via the gas inlet conduit and fluid specimen transported via the fluid specimen outlet of the probe assembly through the valve to clean and purge the barrel and needle, a gas can be injected into the lateral passageway of the fluidic valve to remove the purging fluid from the needle, and the needle of said fluid injector sub-assembly then dried, the valve can then be closed to trap an accurately measured volume of the fluid specimen within the barrel and needle, the slide plate can then be moved forward by actuation of said first piston unit to insert the dispensing end of the needle into the septum inlet of said analytical instrument, and the measured quantity of fluid specimen then injected by activation of said second piston unit which moves the barrel forward relative to the needle to displace and inject the fluid specimen via the dispensing end of the needle into the septum inlet of the analytical instrument.

22. The apparatus of claim 21 wherein, within the magazine subassembly, a wall of the outer large diameter member is notched and carries an L-shaped latch oriented and pivotally secured at the lower end of the longest side of said latch so that the short side of the latch and toe portions are extendable inwardly, the inner small diameter member is grooved such that the toe portion of the L-shaped latch rides therein, such that downward movement of the inner small diameter member presses the toe of the L-shaped latch outwardly to cam the short side of the L-shaped latch inwardly to block and hold the vial in place as the septum thereof is pierced by the fixed probe assembly.

23. The apparatus of claim 22 wherein the inner small diameter tubular member is operatively associated with an actuating piston unit which produces reciprocating movement of said inner small diameter tubular member.

* * * * *